United States Patent [19]

Larkin

[11] 4,415,755

[45] Nov. 15, 1983

[54] NITRILES AND PRIMARY AMINES FROM PRIMARY ALCOHOLS

[75] Inventor: John M. Larkin, Austin, Tex.

[73] Assignee: Texaco Inc., White Plains, N.Y.

[21] Appl. No.: 319,846

[22] Filed: Nov. 10, 1981

[51] Int. Cl.$^3$ ..................... C07C 85/06; C07C 120/00
[52] U.S. Cl. ................................ 564/480; 564/479; 260/465.1
[58] Field of Search ............................. 564/480, 479; 260/465.1

[56] References Cited

U.S. PATENT DOCUMENTS

| | | | |
|---|---|---|---|
| 2,337,421 | 12/1943 | Spence et al. | 260/464 |
| 2,337,422 | 12/1943 | Spence et al. | 260/464 |
| 2,529,923 | 11/1950 | Dickey et al. | 564/479 X |
| 2,609,394 | 9/1952 | Davies et al. | 564/479 |
| 2,795,600 | 6/1957 | Chitwood et al. | 564/480 X |
| 2,848,495 | 8/1958 | Villemey | 564/479 |
| 3,128,311 | 4/1964 | Shirley et al. | 564/480 |
| 4,014,933 | 3/1977 | Boettger et al. | 564/480 X |
| 4,293,716 | 10/1981 | Swift et al. | 564/480 |
| 4,314,084 | 2/1982 | de Pinillos et al. | 564/480 |

FOREIGN PATENT DOCUMENTS 934636 8/1963 United Kingdom ................ 260/464

OTHER PUBLICATIONS

Migrdichian, V., *The Chemistry of Organic Cyanogen Compounds*, ACS Monograph Series, Reinhold, New York, 1947, pp. 168-169.
*Chemical Abstracts,* vol. 83, 1975: 58081g, Japan, Kokai 75-30,804; 3/75; Int. Class C07C.
*Chemical Abstracts,* vol. 83, 1975: 78568z, Japan, Kokai 75-32,113; 3/75; Int. Class C07C.
CA, vol. 87, 1977: 133846y, Jodra, L. G., et al., *Acta Cient. Compostelana,* 1977, 14(1), 85-102.
CA, vol. 88, 1978: 169565r, Zakirov, N. S., et al., *Neftekhimiya,* 1978, 18(1), 75-79.
Card, R. J., et al., "Gas-Phase Synthesis of Nitriles," *The Journal of Organic Chemistry,* vol. 46, No. 4, Feb. 13, 1981, pp. 754-757.

*Primary Examiner*—Paul F. Shaver
*Attorney, Agent, or Firm*—Jack H. Park; Kenneth R. Priem; David L. Mossman

[57] ABSTRACT

Primary alcohols may be treated with ammonia and hydrogen in the vapor phase in the presence of a catalyst containing copper and chromium to produce nitriles and primary amines. The nitriles produced are readily convertible to the same corresponding primary amines. The reaction may be conducted at a temperature in the range of 240° to 320° C. which is substantially lower than the temperatures used in other methods used to make nitriles. Conversions of the alcohols are 95% or higher, and selectivities to the combined primary amines and nitriles are higher than other methods.

8 Claims, No Drawings

NITRILES AND PRIMARY AMINES FROM PRIMARY ALCOHOLS

BACKGROUND OF THE INVENTION

1. Field of the Invention

The invention relates to the catalytic production of nitriles and primary amines from primary alcohols, and more particularly relates to the production of nitriles and primary amines at lower temperatures over a catalyst containing copper and chromium.

2. Description of Related Methods

The production of primary amines from primary alcohols and ammonia would be a very desirable process if it could be performed with high selectivity to the amines. The reductive amination of secondary alcohols proceeds well, but primary alcohols frequently give undesired by-products including secondary amines and hydrogenolysis products. For example, Japanese Pat. No. 75-30,804 (Chemical Abstracts 83: 58081g) relates that a nickel-copper-chromium catalyst may convert ammonia and 1-butanol at a 93% conversion, to n-butyl amine in only 64% selectivity at a temperature of 205° C. and a pressure of 2,275 psig. The same patent reveals that n-dodecanol may be converted to dodecyl amine in 55% selectivity. High conversions would be necessary in a process such as this because of the proximate boiling points of the primary amine and primary alcohol, and therefore the distillation to remove the unreacted alcohol would be difficult. Further, Japanese Pat. No. 75-32113 (C. A. 83: 78568z) teaches that higher selectivity to the primary amine may be achieved but at the expense of conversion. In that patent, the conversion of dodecanol to dodecyl amine is achieved with 95.3% selectivity, but at a 71.7% alcohol conversion. The reaction therein was conducted at 120° to 220° C. under atmospheric pressure using a cobalt catalyst containing magnesium, calcium, zinc, cadmium and/or manganese.

A titanium oxide/molybdenum oxide catalyst yields decyl amine and 1-decene from 1-decanol in the vapor phase according to Takita, Y.; Seyiama, T. and Nishida, Y., Bull. Chem. Soc. Japan, 49 (12), pp 3699–3700, Dec. 1976. In that article, the highest n-decyl amine selectivity achieved was 68.7% at 11.2% conversion.

French Pat. No. 1,302,365, which corresponds to British Pat. No. 934,636, indicates that a nickel catalyst may promote the formation of primary, secondary and tertiary amines from ethylene glycol monomethyl ether in yields of 35, 40 and 3%, respectively. None of these methods has been able to convert primary alcohols to primary amines with both high conversions and high selectivities.

There has been recent work in the vapor phase reductive amination of primary alkanols with secondary amines to produce the corresponding tertiary alcohols in high selectivity. The catalyst employed was copper chromite supported on silica, and other copper catalysts. See, for example: Baiker, A. and Richarz, W., Helv. Chem. Acta, 61, pp 1169–1174 (1978); Baiker, A. and Richarz, W. Synthetic Comm., 8(1), pp 27–32 (1978); Baiker, A. and Richarz, W., Tet. Lett., 1977, pp 1937–38; also Preprints - Can. Symp. Catal., 5th, 1977, Chem. Inst. Can., Ottawa, Ontario, pp 1169–1174; and finally German Offen. No. 2,535,073 issued on Feb. 17, 1977.

Typically, conversions and selectivities are greater than or equal to 97%.

Nitriles have been formed from amines or by the amination of alcohols over various catalysts, but only at higher temperatures than those used in the inventive method. For example, Migrdichian in The Chemistry of Organic Cyanogen Compounds, ACS Monograph No. 105, Reinhold, New York, 1947, p 168 (see also U.S. Pat. Nos. 2,337,421 and 2,337,422) indicates that alkyl amines are converted to nitriles at 320° to 330° C. over nickel catalysts or at 400° to 420° C. over copper catalysts. Alcohols can be converted to nitriles in the presence of ammonia over "dehydrogenation catalysts" at 300° to 400° C. Another group has reported the same reaction over FeS at 450° C., Zakirov, N. S., Absurakhmanov, E. A., and Kusainov, Kh. Sh., (Sammarkand) Neftekhimiya, 1978, 18 (1), 75–9 (C. A. 88: 169565r).

Other workers have used zinc oxide or magnetite as the catalyst, as shown in Jodra, L. G.; Arogan, J. M. and Corella, J., Acta Cient Compostelana, 14 (1), (1977), pp 85–102 (C.A. 87:133846y).

Japanese investigators have reported mixtures of secondary amine, nitrile and hydrocarbons from the treatment of 1-butyl amine with hydrogen over a cobalt-molybdenum-aluminum oxide catalyst at approximately 200° to 500° C., Hattori, T.; Kanetake, K. and Murakami, Y., Nippon Kagaku Kaishi, 1977 (11), pp 1591–96.

Production of nitriles from alcohols or aldehydes at 470° C. over a zinc oxide on aluminum oxide catalyst has been taught in German Offen. No. 1,816,279, issued on July 16, 1970, and French Pat. Nos. 1,550,144 and 1,562,129.

SUMMARY OF THE INVENTION

The invention concerns a method for the continuous production of nitriles and primary amines from primary alcohols by means of reductive amination comprising reacting a primary alcohol with ammonia and hydrogen, all in the vapor phase, in the presence of a dehydrogenation catalyst containing copper.

DETAILED DESCRIPTION OF THE PREFERRED EMBODIMENT OF THE INVENTION

Generally, the invention is practiced by treating primary alcohols with ammonia and hydrogen in the vapor phase. The catalyst used is copper chromite and other related dehydrogenation catalysts. A mixture of primary amines and nitriles is produced, and the nitriles may be converted to primary amines by conventional hydrogenation. The method of this invention has a much higher selectivity to primary amines or materials which may be readily converted to primary amines than the selectivities exhibited by related methods in the field. Also, nitriles may be formed at a substantially lower temperature as compared with the related art methods. It should be noted that although high alcohol conversions are obtained by this method, that secondary amine by-products are produced in very low amounts.

The reactants used in the method of this invention include primary alcohols, ammonia and hydrogen. The primary alcohols should have a boiling point sufficiently low to permit vaporization at temperatures and pressures of desired operation. It is especially preferred that the alcohol has no amine substituent in the beta position; that is, on the second carbon atom counting from the carbon atom with the hydroxyl group.

The catalyst useful in this invention may be a dehydrogenation catalyst, and it is preferred that the catalyst contain copper. It is especially preferred that the catalyst be copper chromite. The catalyst may be supported by any common support material, such as a silica gel.

The reaction may be conducted at a variety of temperatures, however, it is preferred that the temperature be between 240° and 320° C. Also, the pressure may range from one atmosphere or below to several atmospheres. It is important, however, that the conditions be such that the reactants are all in the vapor phase. Generally, the application of pressure will cause the reactants to be in the liquid phase, and as shown in the examples, the product distribution changes toward secondary amines when pressure is applied. It is also especially preferred that the reaction be conducted in a continuous fashion.

It is not unusual to have alcohol conversions on the order of 95% or higher when the method of this invention is employed. It is also not unusual for the combined selectivities to nitrile and primary amine to be 95% or higher.

The hydrogenation of nitriles to primary amines is so conventional it is mentioned in basic organic chemistexts. See, for example, A. Streitwieser, Jr. and C. H. Heathcock, *Introduction to Organic Chemistry*, Macmillan: New York, 1976, pp 781-782. Catalysts which are useful in this hydrogenation include nickel-copper-chromia and cobalt-copper-chromia combinations, especially the latter.

The method of this invention also provides an easier route to the production of 2-methoxyacetonitrile as compared with the method disclosed by P. A. Argabright, et al., *Chemistry and Industry*, 1964 (30), p 1365. The Argabright, et al. method is a difficult route which employs the reaction of sodium cyanide with methylchloromethyl ether to produce the methoxy acetonitrile. Methoxyacetonitrile is an interesting type of bifunctional compound which might be useful for solvent applications, for instance, such as a butadiene extraction solvent. Direct amination of 2-methoxy ethanol is much preferred over using sodium cyanide.

The method of this invention will be further illustrated by the examples which follow.

EXAMPLE I

Amination of 1-Octanol Over Copper Chromite at 245° C.

In a heated one inch ID quartz glass column was placed 100 cc of copper chromite catalyst tablets. A mixture of hydrogen and nitrogen was passed through the catalyst bed maintained at 300°-500° C. in order to activate the catalyst. Then the hot part of the catalyst bed was maintained at 244°-246° C. while a mixture of 1-octanol (0.194 mole/hour), ammonia (3.16 mole/hour) and hydrogen (approximately 180 cc/minute) was passed downward through the tube; effluent was collected in an ice-cooled bath. Gas-liquid chromatography analysis indicated 63.3% conversion of 1-octanol. Selectivities to octane nitrile, 1-amino octane and dioctyl amine were 35.1, 36.3 and 8.5%, respectively. Selectivities do not add up to 100% due to minor amounts of unknowns.

EXAMPLE II

Amination of 1-Octanol Over Copper Chromite at 282° C.

The procedure of Example I was essentially repeated except that the temperature was raised to 282° C. and the 1-octanol feed rate was increased to 0.203 mole/hour. Conversion of 1-octanol was 97.4%; selectivities to nitrile, primary amine and dialkyl amine were 80.9, 15.8 and 0.8%, respectively. Nuclear magnetic resonance analysis confirmed this gas-liquid chromatography result in that proton integration ratios indicated approximately 83% octane nitrile and 17% 1-amino octane. This experiment illustrates the high conversion and high selectivity to primary amine and potential primary amine (nitrile) which is possible with this method.

EXAMPLE III

Amination of 1-Octanol Over Copper Chromite Supported on Silica Gel at 282° C.

The procedure of Example II was essentially repeated except that 95 cc of copper/chromium on silica gel was substituted for the copper chromite. Conversion was 92.2% and selectivities to nitrile, primary amine and dialkyl amine were 81.1, 14.5 and 1.7%. This experiment illustrates the high selectivities but slightly lower activity provided by this catalyst. (The manufacturer lists the CuO and $Cr_2O_3$ content of this catalyst as 22.0% and 1.03%, respectively).

EXAMPLE IV

Amination of 1-Octanol Over Copper Chromite Supported on Silica Gel at 305° C.

When this catalyst was used at 305° C. under the same conditions as in Example III, the 1-octanol conversion was 95.2% and selectivities to nitrile, primary amine and secondary amine were 90.1, 6.7 and 0.6%, respectively.

EXAMPLE V

Amination of 1-Octanol Over Copper Chromite at 115 psig Pressure

The procedure of Example II was repeated with the following differences: only 25 cc of catalyst were used, the catalyst was contained in a stainless steel tube and the contents were maintained at 115 psig total pressure. The 1-octanol feed rate was approximately 0.05 moles/hour, and the temperature was 275° C. The conversion of 1-octanol was 99%; selectivities to nitrile, primary amine and secondary amine were 3.4, 58.2 and 33.5%, respectively. This experiment illustrates the detrimental effect of conducting the amination under pressure as the dioctyl amine constitutes a substantial portion of the product. Under these conditions, the 1-octanol was in the liquid phase, not the vapor phase.

EXAMPLE VI

Amination of 2-Methoxyethanol Over Copper Chromite

The catalyst and procedure of Example I was repeated except that only 60 ml of catalyst was used, 2-methoxyethanol was substituted for 1-octanol, the temperature was 295° C. and the alcohol feed rate was 0.224 moles/hour. The conversion of alcohol was 96.2%; selectivities to methoxyacetonitrile, 2-methoxyethylamine and di-(2-methoxyethyl) amine were 52.8, 16.2 and 8.0%, respectively.

EXAMPLE VII

Amination of 2-Methoxyethanol Over Co/Cu/Cr Catalyst

The procedure of Example VI using a catalyst containing cobalt, copper and chromium at 280° C. resulted in only 14% conversion of methoxyethanol to yield predominantly 2-methoxyethylamine.

These examples and others conducted under similar conditions are summarized in Table I.

TABLE III

METHOXYETHANOL AMINATION IN THE PRESENCE of AMMONIA, HYDROGEN AND COPPER CHROMITE

| Ex. | Temperature C. | Pressure, psig | Mole Ratio $NH_3$/Alc. | Conversion, % | Selectivity, % 1° Amine | 2° Amine | Nitrile |
|---|---|---|---|---|---|---|---|
| 6  | 295 | 0    | 17 | 96 | 16 | 8  | 53 |
| 17 | 275 | 140  | 12 | 93 | 65 | 31 | 0  |
| 20 | 275 | 325  | 12 | 99 | 66 | 25 | 7  |
| 21 | 305 | 325  | 12 | 99 | 57 | 14 | 7  |
| 22 | 275 | 2500 | 12 | 94 | 74 | 24 | 0  |
| 23 | 295 | 2500 | 12 | 95 | 79 | 17 | 0  |

TABLE I

EXAMPLES ILLUSTRATING THE INVENTIVE METHOD

| Ex. | Catalyst[1] | Temp., °C. | Mole Ratio $NH_3$/Alc. | Mole/Hr Alcohol | Pressure, psig | Catalyst, ml | % Conversion | % Selectivity Nitrile | Primary Amine | Secondary Amine |
|---|---|---|---|---|---|---|---|---|---|---|
|   |   |   |   |   | 1-octanol |   |   |   |   |   |
| 1  | A  | ~245 | 16.3 | 0.194 | None | ~110 | 63.3 | 35.1 | 36.3 | 8.5 |
| 2  | A  | ~282 | 15.6 | 0.203 | None | ~110 | 97.4 | 80.9 | 15.8 | 0.8 |
| 3  | B  | ~282 | 15.6 | 0.203 | None | 95   | 92.2 | 81.1 | 14.5 | 1.7 |
| 4  | B  | ~305 | 15.6 | 0.203 | None | 95   | 95.2 | 90.1 | 6.7  | 0.6 |
| 8  | A  | ~290 | 20.6 | 0.154 | None | ~60  | 92.7 | 65.5 | 27.6 | 3.5 |
| 9  | B  | ~245 | 16.8 | 0.189 | None | 95   | 84.6 | 60.1 | 24.3 | 11.6 |
| 5  | A  | 275  | 15.1 | ~0.05 | ~115 | 25   | 99.0 | ?3.4[2] | 58.2 | 33.5 |
| 10 | A  | 260  | 15.1 | ~0.05 | ~115 | 25   | 98.0 | ?1.7 | 60.2 | 31.3 |
| 11 | A  | 245  | 15.1 | ~0.05 | ~115 | 25   | 98.0 | ?3.8 | 60.5 | 25.4 |
|    |    |      |      |       | methoxyethanol |   |   |   |   |   |
| 6  | A  | ~295 | 17.5 | 0.224 | None | 60   | 96.2 | 52.8 | 16.2 | 8.0 |
| 7  | C  | 280  | 17.5 | 0.224 | None | 60   | 14.0 | —    | >50.0 | — |
| 12 | B  | ~325 | 8.9  | 0.358 | None | 95   | 16.0 | 53.6 | 23.4 | ?6.5 |
| 13 | B[3] | ~292 | 9.2  | 0.343 | None | 95   | ~5.0 | 35.7 | 35.0 | ?8.7 |
| 14 | B[4] | ~290 | 17.5 | 0.224 | None | ~110 | 63.5 | 65.9 | 28.1 | ?1.5 |
| 15 | B[3] | ~345 | 14.8 | 0.265 | None | ~110 | 18.4 | 60.8 | 4.2  | ?4.4 |
| 16 | A  | 260  | 12.0 | ~0.07 | 140  | 25   | 94.1 | <21.9 | >45.7 | 27.8 |
| 17 | A  | 275  | 12.0 | ~0.07 | 140  | 25   | 92.7 | 0.0  | 65.3 | 30.8 |
| 18 | A  | 300  | 12.0 | ~0.07 | 140  | 25   | 90.5 | 0.0  | 72.0 | ?7.8 |
| 19 | A  | 325  | 12.0 | ~0.07 | 140  | 25   | 92.9 | 0.0  | 56.9 | ?10.4 |

[1]Catalysts: A = copper chromite, B = copper chromite on silica gel, C = Co/Cu/Cr
[2]Question mark means identity and selectivity are uncertain.
[3]Used catalyst
[4]Fresh catalyst At atmospheric pressure, the nitrile and primary amine appear to equilibrate. In two separate runs at 290° C., 1-octanol and 1-octyl amine produced nearly identical product ratios. See Table II below.

TABLE II

| EQUILIBRATION EVIDENCE | | | |
|---|---|---|---|
|   | % Composition | | |
| Feed | Octane Nitrile | Octyl Amine | Dioctyl Amine |
| 1-octanol   | 65 | 28 | 4 |
| 1-octylamine | 66 | 27 | 6 |

Conducting the reaction under hydrogen pressure shifts the equilibrium in favor of the amine, and apparently the product amine can condense with the nitrile more easily than ammonia. Since the operating temperature is well above the critical temperature of ammonia, the reaction between nitrile and primary amine (both in the liquid phase when conducted under pressure) is favored.

This pressure effect was checked using methoxyethanol amination. The reaction was conducted at 0, 140, 325 and 2,500 psig. Yield of products are listed in Table III below.

The dramatic effect of pressure is evident from Table III with nitrile production dropping to virtual nonexistence with only a modest pressure increase. The combined yield of primary amine and nitrile (potentially a primary amine) also decreases with pressure. At the highest temperature shown in Table III (305° C.), unknown compounds made a relatively large contribution, so total selectivities were down. See also Table I, Examples 5, 9 through 11 and 16 through 19.

Copper chromite seems to be unique in promoting nitrile formation at relatively low temperatures. Other types of copper chromite, such as copper/chromite on silica gel, appeared less active and lost their activity faster than copper chromite. Sometimes after prolonged idle time, even the copper chromite appeared to deactivate.

The cobalt-copper-chromium catalyst used in Example VII is not a preferred catalyst for vapor phase conversion of primary alcohols to amines. At about 280° C. and one atmosphere, conditions under which copper chromite gives good conversions, only a 14% conversion of methoxyethanol, predominantly to methoxyethylamine was realized.

Diethylene glycol (DEG) and N,N-dimethylethanolamine (DME) do not appear as suitable for conversion to primary amines with ammonia and hydrogen over copper chromite as does methoxyethanol. At 305°

C., DEG at atmospheric pressure undergoes less than 50% conversion to a large number of products. At 260°-310° C. and pressures of 160-500 psig, which are vapor phase conditions, DME undergoes good conversions (greater than 95%), but the selectivity to any one product is poor. N,N-Dimethylethylenediamine appears to be the largest single component, but it is produced in no better than about 25% under any of the conditions tried. Operating data for the DME aminations are shown in Table IV.

TABLE IV

| | | DME AMINATION | | | | |
|---|---|---|---|---|---|---|
| Ex. | Catalyst | Temp. °C. | Mole Ratio NH$_3$/DME | Mole/Hr DME | Pressure, psig | ml, cat. | % Conversion |
| 24 | Cu/Cr/SiO$_2$ | 270 | 17.3 | 0.226 | None | ~110 | ~9 |
| 25 | Cu/Chromite | 260 | 15.0 | 0.0669 | 160 | 24 | 98 |
| 26 | " | 280 | 15.0 | 0.0669 | 160 | 24 | 96 |
| 27 | " | 300 | 15.0 | 0.0669 | 160 | 24 | 97 |
| 28 | " | 250 | 15.0 | 0.0669 | 325 | 24 | 90 |
| 29 | " | 265 | 15.0 | 0.0669 | 325 | 24 | |
| 30 | " | 280 | 15.0 | 0.0669 | 325 | 24 | |
| 31 | " | 295 | 15.0 | 0.0669 | 325 | 24 | |
| 32 | " | 310 | 15.0 | 0.0669 | 325 | 24 | |

EXAMPLE 33

The reason for the poor selectivity to N,N-dimethylethanolamine, especially at low pressures, is probably related to initial formation of N,N-dimethylacetonitrile. At high temperatures it may decompose to dimethyl amine, formaldehyde and hydrogen cyanide (a reverse Strecker reaction). Evidence of this behavior was found during atmospheric pressure amination of hydroxyethylmorpholine. At 275° C., only 31% conversion was achieved. The main products were morpholine (77% selectivity), N-methylmorpholine (10%) and cyanomethylmorpholine (6%). Hydrogen cyanide and methanol were identified in the off-gas.

From Examples 24 through 33 it may be seen why it is preferred that there be no amine substituents in the beta position of the primary alcohol.

Many modifications may be made in the method of this invention without departing from its scope which is defined only by the appended claims. For example, it would be expected that one skilled in the art could change the temperature or find another dehydrogenation catalyst containing copper which would optimize the yield.

I claim:

1. A method for the continuous production of nitriles and primary amines from primary alcohols by means of reductive amination comprising
   reacting a primary alcohol having no amine substituents in the beta position, with ammonia and hydrogen, all in the vapor phase, in the presence of a copper chromite catalyst.

2. The method of claim 1 in which the reaction is conducted at a temperature in the range of about 240° to about 320° C.

3. The method of claim 1 in which the alcohol conversion is 95 percent or more and the combined selectivities to primary amine and nitrile are 95 percent or more.

4. The method of claim 1 in which the nitrile component of the product is subsequently hydrogenated to the corresponding primary amine.

5. A method for the continuous production of nitriles and primary amines from primary alcohols by means of reductive amination comprising
   reacting a primary alcohol which has no amine substituents in the beta position with ammonia and hydrogen, all in the vapor phase, at a temperature in the range of about 240° to about 320° C. in the presence of a copper chromite dehydrogenation catalyst in which the alcohol conversion is 95 percent or more and the combined selectivities to primary amine and nitrile are 95 percent or more.

6. The method of claim 5 in which the nitrile component of the product is subsequently hydrogenated to the corresponding primary amine.

7. A method for the continuous production of primary amines from primary alcohols by reductive amination comprising
   (a) conditioning a dehydrogenation catalyst consisting of copper chromite by passing hydrogen gas over the catalyst at a temperature in the range of about 300° to 350° C.,
   (b) passing a reactant gas over the catalyst at a temperature in the range of about 240° to about 320° C., the reactant gas comprising
      (i) a primary alcohol having no amine substituents in the beta position, and
      (ii) ammonia, such that 95 percent or more of the alcohol is converted,
   (c) cooling and condensing the product gas to a mixture where 95 percent or more of the mixture is nitrile or primary amine,
   (d) separating out and hydrogenating that part of the mixture which is nitrile to convert it to the same primary amine that remained in the mixture, and
   (e) re-combining the two portions of primary amine.

8. The method of claim 7 in which the nitrile hydrogenation is conducted over nickel-copper-chromia or a cobalt-copper-chromia hydrogenation-dehydrogenation catalyst.

* * * * *